(12) United States Patent
Morrison et al.

(10) Patent No.: US 10,129,956 B2
(45) Date of Patent: Nov. 13, 2018

(54) PRESENCE BASED ILLUMINATION AND ANALYTICS SYSTEM

(71) Applicant: Luna Lights, Inc., Chicago, IL (US)

(72) Inventors: Donovan Morrison, Chicago, IL (US); Matt Wilcox, Chicago, IL (US); Wesley Youman, Chicago, IL (US)

(73) Assignee: Luna Lights, Inc., Chicago, IL (US)

( * ) Notice: Subject to any disclaimer, the term of this patent is extended or adjusted under 35 U.S.C. 154(b) by 0 days.

(21) Appl. No.: 15/531,419

(22) PCT Filed: Dec. 17, 2015

(86) PCT No.: PCT/US2015/066467
§ 371 (c)(1),
(2) Date: May 26, 2017

(87) PCT Pub. No.: WO2016/100718
PCT Pub. Date: Jun. 23, 2016

(65) Prior Publication Data
US 2017/0332459 A1    Nov. 16, 2017

Related U.S. Application Data

(60) Provisional application No. 62/092,869, filed on Dec. 17, 2014.

(51) Int. Cl.
*G08B 23/00* (2006.01)
*H05B 37/02* (2006.01)
(Continued)

(52) U.S. Cl.
CPC ....... *H05B 37/0227* (2013.01); *A61B 5/6892* (2013.01); *G05B 15/02* (2013.01);
(Continued)

(58) Field of Classification Search
CPC .. H05B 37/0227; G08B 21/22; A61B 5/6892; A61B 2562/0247
(Continued)

(56) References Cited

U.S. PATENT DOCUMENTS 4,633,237 A * 12/1986 Tucknott ............... A61B 5/6892
340/525
2003/0216670 A1* 11/2003 Beggs .................... G08B 21/22
600/595

(Continued)

OTHER PUBLICATIONS

Beddit. "Sleep Monitor" www.beddit.com, Dec. 19, 2014 (accessed via Wayback Machine at web.archive.org/web/20141219110912/http:/www.beddit.com/), 3 pages.
(Continued)

*Primary Examiner* — John A Tweel, Jr.
(74) *Attorney, Agent, or Firm* — Lee Sullivan Shea & Smith, LLP

(57) ABSTRACT

Disclosed herein are systems, devices, and methods relating to presence based detection and analytics including detecting a first movement associated with a bed; based on the first movement, sending a first signal to turn on at least one light and sending a second signal indicative of the first movement; detecting a second movement associated with the bed; and based on the second movement, sending a third signal to turn off at least one light and sending a fourth signal indicative of the second movement.

20 Claims, 6 Drawing Sheets

(51) Int. Cl.
    *A61B 5/00*         (2006.01)
    *G08B 21/22*     (2006.01)
    *G06Q 50/22*     (2018.01)
    *G06Q 50/24*     (2012.01)
    *G06Q 10/06*     (2012.01)
    *G16H 40/63*     (2018.01)
    *G05B 15/02*     (2006.01)
    *G06F 19/00*     (2018.01)

(52) U.S. Cl.
CPC .............. *G06F 19/00* (2013.01); *G06Q 10/06* (2013.01); *G06Q 50/22* (2013.01); *G06Q 50/24* (2013.01); *G08B 21/22* (2013.01); *G16H 40/63* (2018.01); *H05B 37/0245* (2013.01); *H05B 37/0281* (2013.01); *A61B 2562/0247* (2013.01); *H05B 37/0236* (2013.01)

(58) Field of Classification Search
USPC ....................................................... 340/573.1
See application file for complete search history.

(56) References Cited

U.S. PATENT DOCUMENTS

| | | | | |
|---|---|---|---|---|
| 2005/0258954 | A1* | 11/2005 | Ruskin | F21V 23/0442 340/527 |
| 2008/0169931 | A1* | 7/2008 | Gentry | G08B 21/22 340/573.1 |
| 2012/0154155 | A1* | 6/2012 | Brasch | G08B 21/22 340/573.4 |

OTHER PUBLICATIONS

Beddit. "Science Behind Beddit" www.beddit.com/science/, Oct. 14, 2014 (accessed via Wayback Machine at web.archive.org/web/20141014104528/http:/www.beddit.com/science/), 3 pages.

Smart Caregiver Corporation. "Quiet Fall Prevention & Mobility Monitoring" smartcaregiver.com Dec. 16, 2014 (accessed via Wayback Machine at web.archive.org/web/20141216020928/http:/smartcaregiver.com/), 5 pages.

Smart Caregiver Corporation. "Fall Prevention Monitors." Dec. 16, 2014 (accessed via Wayback Machine web.archive—, 5 pages.

* cited by examiner

PRESENCE BASED ILLUMINATION AND ANALYTICS SYSTEM

CROSS REFERENCE TO RELATED APPLICATION

This application is a national phase patent application of, and claims priority to, PCT International Application No. PCT/US15/66467, filed on Dec. 17, 2015, and entitled "PRESENCE BASED ILLUMINATION AND ANALYTICS SYSTEM," which claims priority to U.S. Provisional Application Ser. No. 62/092,869, filed on Dec. 17, 2014, and entitled "A System and a Method for Fall Prevention and Detection." The contents of each of the above-referenced applications are incorporated herein by reference in its entirety.

FIELD OF THE DISCLOSURE

This disclosure is related to the health care industry and more particularly to methods, systems, products, features, services, and other elements for providing a presence based illumination and analytics system.

BACKGROUND

Various systems exist for maintaining a safe home environment especially for the elderly and disabled. The systems are typically designed to allow for independent living while reducing the chances for injury.

Lighting systems is one mechanism for improving safety within the home. The lighting systems provide illumination so as to ensure safe mobility. For example, standard night lights may be plugged into wall outlets to provide a suitable illumination at night. These lights are placed in power outlets or receptacles on walls and are kept switched on throughout the night. Another example is motion-sensor lights which are activated upon detection of motion and are turned off when the motion ceases for a preset amount of time. Still another example is infrared and pressure sensor triggered lights. Infrared triggered lights are turned on when an infrared beam is tripped and turned off after a preset amount of time. Pressure sensor triggered lights are turned on and off based on a pressure applied to a pressure sensor, such as a pressure mat on which someone may walk on to trigger the light to turn on and off.

Motion sensors and wearable devices is another a mechanism for improving safety within the home. The motion sensors can be placed in certain locations within the home to detect presence of a person and also detect certain types of movement. Similarly, the wearable devices, worn by a person, can monitor a person's location and type of movement. The person being at certain locations of the home, such as in the bathroom, and/or performing certain types of movements, such as walking may be considered normal, but being in other locations and/or performing other types of movements may be considered abnormal. For example, the motion sensors and wearable devices can detect if the person is in the street of his or her home, the person is immobile, or the person has fallen and cannot get up. In this situation, the person may be injured or need help. In this case, an alert signal could be sent so that a caregiver or other interested person can check up on the condition of the person.

Such systems allow for the elderly and disabled to lead safe, independent, and normal lives.

SUMMARY

In an embodiment, a method comprises detecting a first movement associated with a bed; based on the first movement, sending a first signal to turn on at least one light and sending a second signal indicative of the first movement; detecting a second movement associated with the bed; and based on the second movement, sending a third signal to turn off at least one light and sending a fourth signal indicative of the second movement. The method of detecting the first movement comprises determining that a person is not on the bed and detecting the second movement comprises determining that the person is on the bed. The method of sending the second and fourth signal results in a determination of a duration of time that the person is not on the bed. The method of detecting the first movement and second movement comprises receiving signals from a sensor placed in the bed. The second signal may be indicative of a person not on the bed and the fourth signal is indicative of the person on the bed. The second signal may further define a time associated with the first movement and wherein the fourth signal further defines a time associated with the second movement. The method of sending the second signal comprises sending the second signal over a network for storage in a database. The method of sending the second signal results in a determination of a frequency of times that a person gets up from the bed and returns back to the bed.

In another embodiment, a method comprises: receiving, from a controller connected to a sensor on a bed, one or more signals indicative of a movement associated with a bed; and based on the one or more signals, determining a duration that a person is not on the bed. The one or more signals may indicate that the person is not on the bed. The method further comprises sending an alert when the duration exceeds a threshold amount. The method further comprises determining, based on the signals, a frequency of times that a person gets up from the bed and returns back to the bed. The method of determining a duration that a person is not on the bed comprises starting a timer based on the one or more signals.

In yet another embodiment, a controller comprises: a first interface for sending signals to a first network; a second interface for sending signals to at least one light over a second network; a processor comprising instructions, which when executed, cause the processor to: detect a first movement associated with a bed; based on the first movement, send a first signal over the first network to turn on the at least one light and send a second signal indicative of the first movement over the second network; detect a second movement associated with the bed; based on the second movement, send a third signal over the first network to turn off at least one light and send a fourth signal indicative of the second movement over the second network. The instructions for detecting the first movement comprises determining that a person is not on the bed and the instructions for detecting the second movement comprises determining that the person is on the bed. The instructions for sending the second and fourth signal results in a determination of a duration of time that the person is not on the bed. The instructions for detecting the first movement and second movement comprises receiving signals from a sensor placed in the bed. The sensor may be a capacitive sensor placed in the bed. The sensor may be a pressure sensor placed in the bed. The sensor may be placed on an upper half of the bed.

BRIEF DESCRIPTION OF THE DRAWINGS

Features, aspects, and advantages of the presently disclosed technology may be better understood with regard to the following description, appended claims, and accompanying drawings where:

Figure 1:
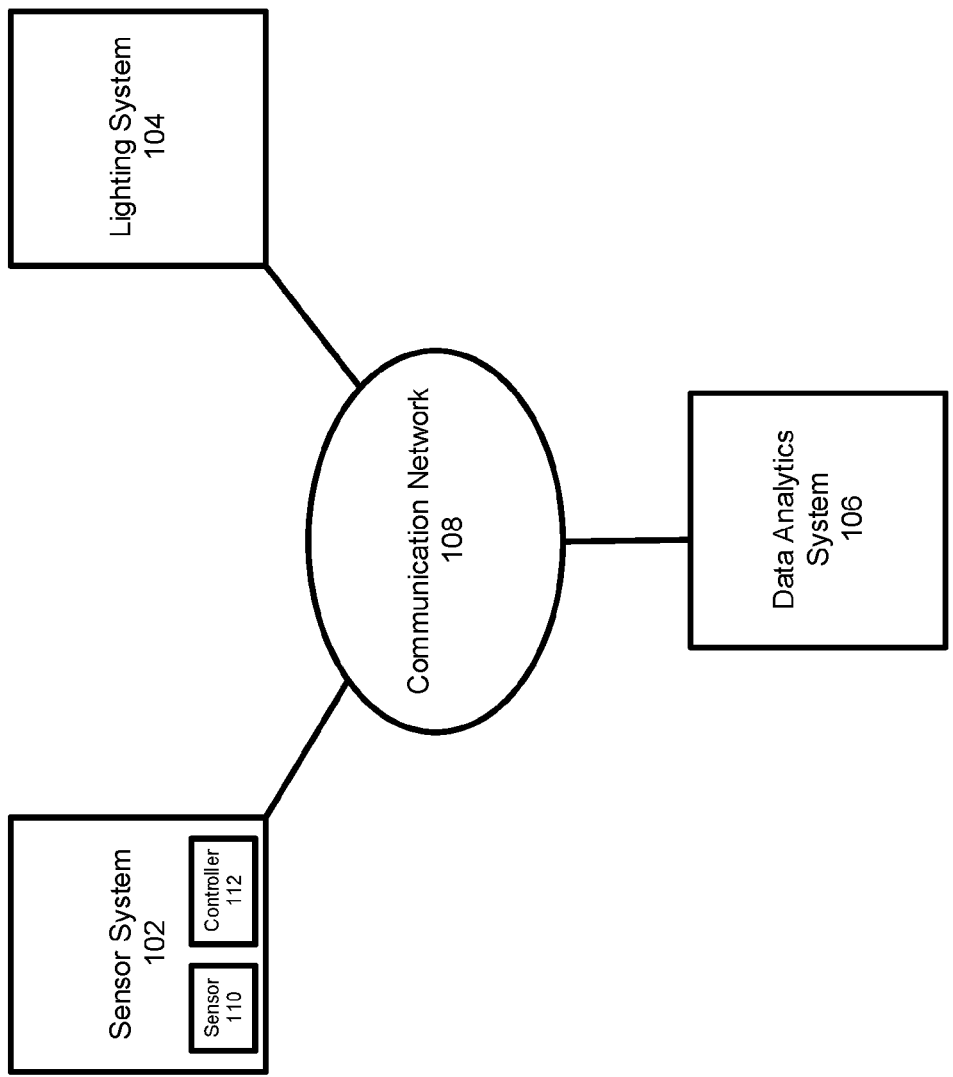
FIG. 1 illustrates an example block diagram of the presence-based illumination and analytics system.

The drawings are for the purpose of illustrating example embodiments, but it is understood that the embodiments are not limited to the arrangements and instrumentality shown in the drawings.

DETAILED DESCRIPTION

The following disclosure makes reference to the accompanying figures and several exemplary scenarios. One of ordinary skill in the art will understand that such references are for the purpose of explanation only and are therefore not meant to be limiting. Part or all of the disclosed systems, devices, and methods may be rearranged, combined, added to, and/or removed in a variety of manners, each of which may be contemplated herein.

FIG. 1 illustrates an example block diagram of the presence-based illumination and analytics system. The presence-based illumination system may include a sensor system 102, a lighting system 104, and a data analytics system 106 which are communicatively coupled via a communication network 108.

The sensor system 102 may detect a presence of a person. The presence can take many forms and could be in various locations.

For instance, the presence could be movement of a person on a bed. The movement may include, but is not limited to, whether a person is on the bed, not on the bed, is lying down on a bed, is sitting up on the bed, gets up from the bed, is sitting down on the bed, or is rolling around on a bed. Further, the sensor system 102 can detect a weight, heartbeat, and respiratory rate of a person on the bed.

The sensor system 102 may be located on or in proximity to the bed and include a sensor 110 and a controller 112. In one example, the sensor 110 may be a flexible pressure sensitive strip capable of detecting variations in pressure and generate associated electrical signals. The pressure sensitive strip may be further housed in a water-resistant housing. The pressure sensitive strip may be located under the bed sheets of the bed and specifically be placed between the middle and upper part of the bed where a person's head may rest when he or she sleeps. In this regard, the pressure sensor 110 may be placed in line or centered with a person's body, e.g., the back, when he or she lies down in bed. In another example, the sensor 110 may be a flexible capacitive sensitive strip. The capacitive sensor may be located on the bed in a manner similar to the pressure sensitive strip and also housed in a water-resistant housing. The capacitive sensor may detect changes in capacitance between two electrodes and generate associated electrical signals. The sensor 110 may take other forms as well.

The controller 112 may be hardware, software, or a combination of hardware and software coupled to the sensor 102 to receive the electrical signals generated by the sensor 110, determine based on the electrical signals a type of the presence, and take an appropriate action. [24] One action that the controller 112 may take is to activate or deactivate the lighting system 104 when the presence is movement on a bed. Lighting system 104 may comprise one or more light, such as small, portable lights, that provide illumination when activated. The lighting system 104 may be mounted on a wall. The controller 112 and lighting system 104 may communicate via a wired or wireless connection. In this regard, the controller 112 may send a signal to the lighting system 104 to turn on and turn off the lighting system 104 based on the type of detected movement. The controller 112 may send a signal to activate the light when the controller 112 determines, based on the electrical signals from the sensor 110, that a person is not on the bed. The lights may be kept on until the controller 112 determines, based on the electrical signals from the sensor 110, that the person returns to the bed, e.g., is lying down or sitting on the bed. Then, the controller 112 may send a signal to turn off the lighting system 104. This way, a person can move within his or her home having the safety of illumination while out of bed.

Figure 2:
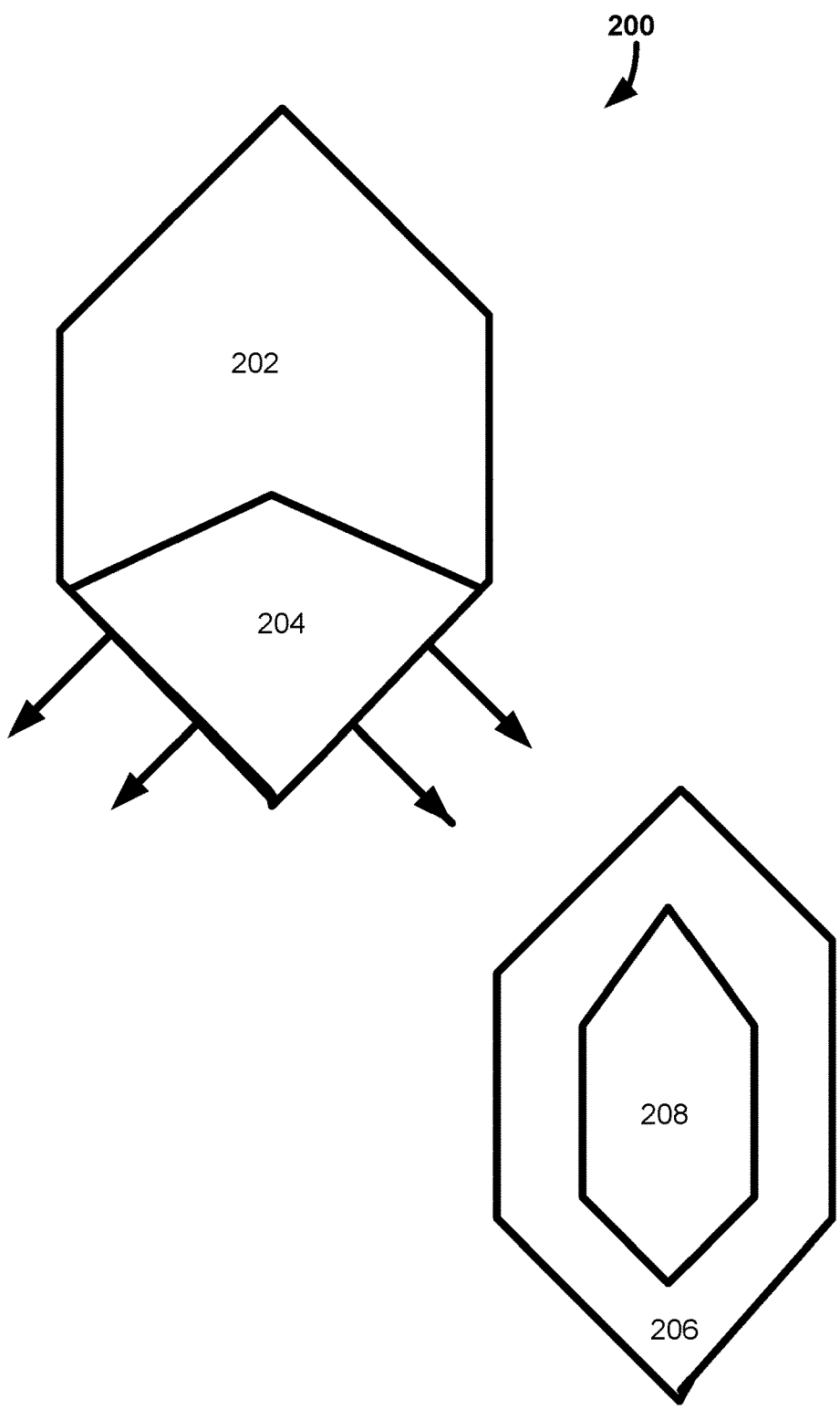
FIG. 2 illustrates an example of a housing of the lighting apparatus.

FIG. 2 is an example of a housing 200 of a lighting apparatus of the lighting system 104. The lighting apparatus may be a battery powered or plugged light source. One or more of the lighting apparatus may guide the user to their night time destination, such as the bathroom. The housing 200 of the lighting apparatus may comprise an opaque surface 202 and a translucent surface 204. The arrangement of the opaque surface 202 and translucent surface 204 may result in a soft glow directed downwards when illuminated by a light inside the lighting apparatus. The housing 200 of the lighting apparatus may be mounted on a fixed surface such as a wall. The housing 200 may be directly attached to the wall or may mate with mounting apparatus 206 which in turn is attached to the wall. In this regard, a portion 208 of the mounting apparatus 206 may mate with a backside of the housing 200 and secure the lighting apparatus to the wall. The portion 208 may be a hook or shoulder, for example. This allows for the lighting apparatus 200 to easily be removed, for example, for battery change or maintenance, while the mounting apparatus 206 retains a bond to the fixed surface.

Referring back to FIG. 1, another action that the controller 112 may take is to send an indication of the type of presence to the data analytics system 106. For example, the controller may send a message which indicates the type of movement on the bed, e.g., a person has sat up, a person has lied down, a person is not on the bed, a person is rolling around on the bed, to the data analytics system 106. Additionally, the message could indicate a time when the movement occurred.

The data analytics system 104 may track movement of the person based on these messages. For instance, based on the messages, the data analytics system 104 may track a time interval for which a person leaves the bed to returning back to the bed and how many times, e.g., a frequency, the person is in and out of bed. By providing a tracking mechanism, the health of a person can be monitored. For instance, if a person does not return to his or her bed after a threshold amount of time, then the person may have fallen down and therefore, an alert can be sent to a caregiver or any interested individual to check up on the person. Additionally, underlying health issues, and the like can be detected by the frequency by which the person gets up and then returns to bed during the night. If the person is going to the restroom more often than normal, this may indicate a health issue, such as a urinary tract infection or improper medication, and preventative action may be taken. Similarly, the data analytics system 106 may provide an appropriate alert to a doctor, for instance.

In other arrangements, the controller 112, itself, may track a time interval for which a person is out of bed or in bed, and determine how many times the person is in and out of bed instead of or in addition to the data analytics system 106. In this case, the controller 112 may not send any messages to the data analytics system 106, send an alert only when a person does not return to bed after a threshold amount of time, or send periodic reports which indicate the movement of the person for a defined time interval. Other arrangements are also possible.

The communication network 108 may include one or more computing systems and network infrastructure configured to facilitate transferring data between the sensor system 102, lighting system 104, and data analytics system 106. The communication network 108 may be or may include one or more Wide-Area Networks (WANs) and/or Local-Area Networks (LANs) and/or wired and/or wireless connections or networks. In some examples, the communication network 108 may include one or more cellular networks and/or the Internet, among other networks. The communication network 104 may operate according to one or more communication protocols, such as LTE, RF, CDMA, WiMax, WiFi, Bluetooth, Zigbee, HTTP, TCP, and the like. Although the communication network 108 is shown as a single network, it should be understood that the communication network 108 may include multiple, distinct networks that are themselves communicatively linked. The communication network 108 could take other forms as well.

Figure 3:
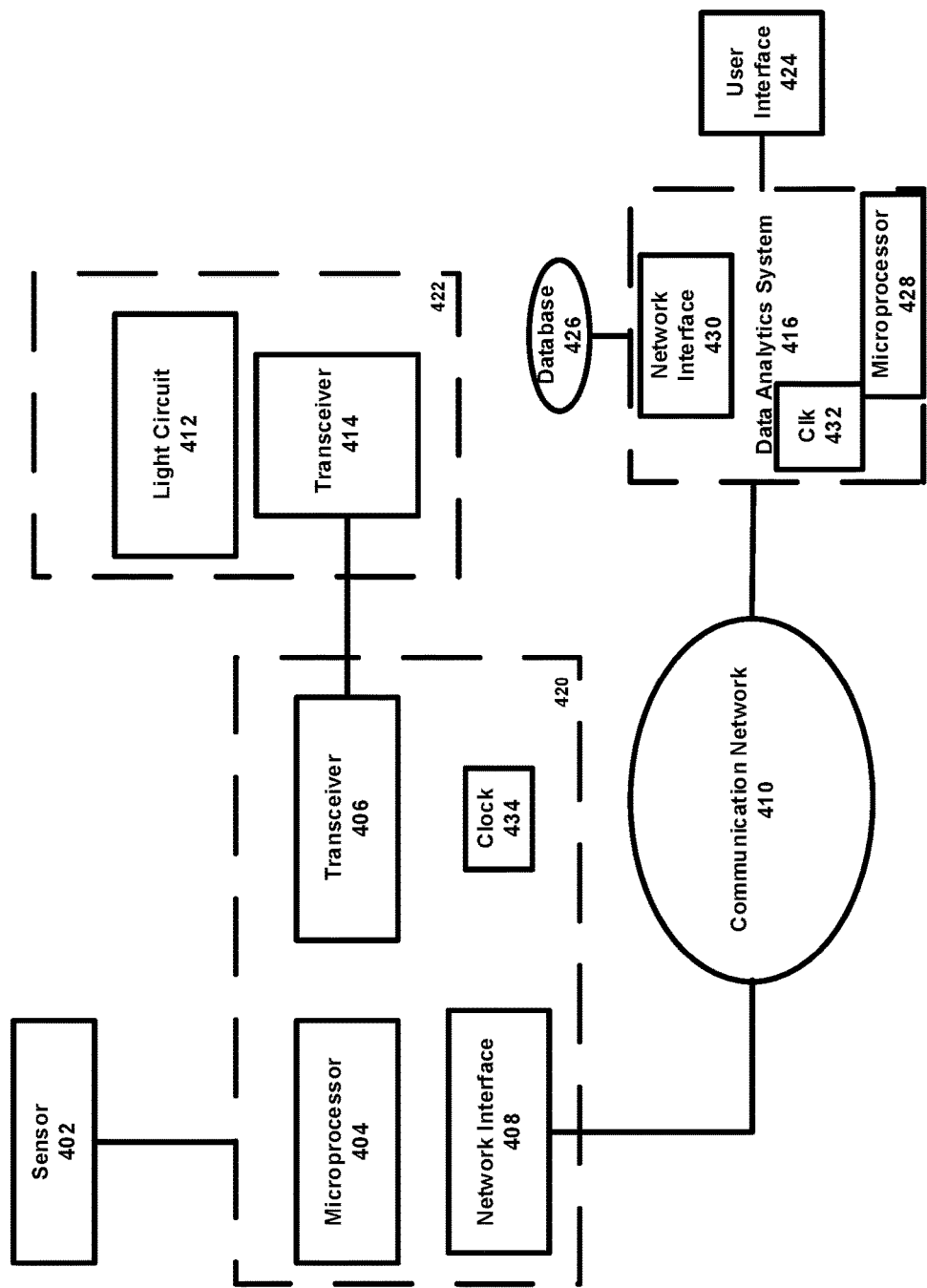
FIG. 3 illustrates an example hardware diagram of the presence-based illumination and analytics system.

FIG. 3 illustrates an example hardware diagram of the presence-based illumination and analytics system. The presence-based illumination and analytics system includes the sensor 402, controller 420, communication network 410, data analytics system 416, and lighting system 422.

The sensor may 402 may be arranged to detect movement on a bed. The sensor 402 may be placed in the bed, e.g., between the sheets of the bed, to detect the movement within the bed. The sensor 402 may take many forms. In one example, the sensor 402 may be a Force Resistive Sensor (FSR) pressure sensing strip with a flexible base layer to detect a variation in pressure due to a person sleeping and getting up from the bed. The FSR pressure sensing strip may measure pressure changes by a changing level of electrical resistance based on the level of pressure applied to the FSR. The FSR pressure sensing strip may output an analog or digital signal to the controller 420 indicative of the pressure changes. Accordingly, when a person lies down on the bed or gets up from the bed, the FSR pressure sensing strip may measure the pressure change and output an associated signal. The signal may be indicative of movement on the bed. In another example, the sensor 402 may be a capacitive sensor. The capacitive sensor may include a dielectric layer, such as made from polyethylene terephthalate (PET), a sensor layer, and a flexible base layer. The sensor layer may include sensor electrodes separated by a distance. The capacitive sensor may measure a change in capacitance as between the sensor electrodes and output an analog or digital signal indicative of the capacitive change. Accordingly, when a person lies down on the bed or gets up from the bed, the capacitive sensor may measure the change in capacitance and output an associated signal. The signal may be indicative of movement on the bed.

The lighting system 422 includes a light circuit 412 and a transceiver 414. The light circuit 412 may include a lighting source such as an incandescent or LED light and circuitry associated with illumination of the light source, such as a processor, battery, and/or wall outlet plug. The transceiver 414 may have a transmitter and receiver so as to transmit and receive signals between the controller 420 and the lighting system 422 to turn on and off the light of the lighting system 422. The signals may take the form of wireless radio frequency (RF) signals or wired signals.

The controller 420 may be coupled to both the sensor 402 and lighting system 422 and facilitate interactions with the sensor 402 and lighting system 422. The controller 420 may have a device identification (device ID) that may uniquely identify the controller 420 and therefore be associated with a person being monitored. The controller 420 may be directly attached to the sensor 402 or connected by a wire. For convenience, the controller 420 may be wirelessly coupled to the lighting system 422. The controller 420 may be powered by a plug receiving power from a wall outlet. In turn, the controller 420 may power the sensor 402.

The controller 420 may include a microprocessor 404, network interface 408, clock 434, and transceiver 406.

The microprocessor 404 may take the form of a general or special-purpose processor. Examples of processors may include microprocessors, application-specific integrated circuits, digital signal processors, and the like. The processor 404 may have an arithmetic processing logic and be capable of executing computer instructions stored on a tangible, non-transitory, medium.

The sensor 402 may send signals indicative of movement on the bed. The microprocessor 404 may receive these signals from the sensor 402 and determine based on the signal a type of movement on the bed. The type of movement may include, but is not limited to, a person not on the bed, on the bed, lying down on the bed, sitting on the bed, or rolling around on the bed.

In order for the microprocessor 404 to make a determination of the type of movement, the microprocessor 404 may need to determine baselines for when a person is not on the bed, lying down on the bed, sitting on the bed, or rolling around on the bed. These baselines may be established during a calibration phase. As one example, a person may be on the bed and the microprocessor 404 may determine the electrical signal generated by the sensor 402 associated with this condition. As another example, a person may be sitting on the bed and the microprocessor 404 may determine the electrical signal generated by the sensor 402 associated with this condition. As yet another example, a person may not be on the bed and the microprocessor 404 may determine the electrical signal generated by the sensor associated with this condition. As yet another example, the baselines may be input to the microprocessor 404 rather than being determined during a calibration stage. General ranges of electrical signals indicative of the types of movements may be provided. Other arrangements are also possible.

The microprocessor 404 may then detect the type of movement based on the signal provided by the sensor 402. For example, the microprocessor 404 may determine from the signal provided by the sensor 402 and the baseline that a person is lying down on the bed. Then, when a person sits up, the microprocessor 404 can determine this type of movement based on the signal from the sensor 402 and/or change in the signal from the sensor 402.

Further, the microprocessor 404 may detect that the person is not on the bed. The microprocessor 404 may maintain a state variable that indicates this condition and output a signal to the lighting system 422 based on this detection. The signal may cause one or more lights of the lighting system 422 to turn on. The transceiver 406, arranged in a manner similar to transceiver 414, may send an RF signal to the lighting system 422 to turn on the light of the lighting system 422. Similarly, when the microprocessor 404 detects a type of movement indicative of the person sitting down or lying down on the bed (after leaving the bed), then the microprocessor 404 may output a signal to the lighting system 422 to turn off one or more lights of the lighting system 422. The microprocessor 404 may determine that the person returned back to the bed because the state variable previously indicated that the person was out of the bed. The microprocessor 404 may also update the state variable to indicate that the person has returned to the bed. This way a person has illumination when out of the bed but not when on the bed.

The controller 420 may also communicate with a data analytics system 416 via the communications network 410. The network interface 408 may facilitate wireless and/or wired communication between controller 420 and data analytics system 416. As such, network interface 408 may take any suitable form for carrying out these functions, examples of which may include an Ethernet interface, a WiFi interface, a Zigbee interface, a Bluetooth interface, a serial bus interface (e.g., Fire-wire, USB 2.0, etc.), a chipset and antenna adapted to facilitate wireless communication, and/or any other interface that provides for wired and/or wireless communication. The network interface 408 may enable wireless communication separately from the wireless communication associated with the transceiver 406. In this regard, the transceiver 406 may not rely on the communication network 410 associated with network interface 408 to turn on and off the lighting system 422. Of course, in other arrangements, communications with the lighting system 422 and data analytics system 416 may be carried out on a single communications network and the functionality of the RF transceiver 406 may be integrated with the network interface 408.

The data analytics system 416 may be a combination of hardware and/or software for managing data associated with the person being monitored. The data analytics system 416 may be a cloud based service residing on a server in the communication network 410 and accessible via a computer or mobile device. Alternatively, the data analytics system 416 may be implemented a computer or mobile device communicatively coupled to the communication network 410. Further, the data analytics system 416 may be located locally or remote to the person being monitored.

The data analytics system 416 may include a microprocessor 428 for executing computer instructions stored on a tangible, non-transitory medium, a network interface 430 for communicating over the communication network 410, and a clock 432 for maintaining timing information. The data analytics system 416 may have access to a database 426 and a user interface 424. In some embodiments, the clock 432 may be configured as a timer.

The database 426 may be used for storing the data associated with the person being monitored and a user interface 424. The database 426 may comprise one or more non-transitory computer-readable storage mediums, examples of which may include volatile storage mediums such as random access memory, registers, cache, etc. and non-volatile storage mediums such as read-only memory, a hard-disk drive, a solid-state drive, flash memory, an optical-storage device, etc. The database 426 may be connected to the data analysis system 416 (as shown in FIG. 3) or may be cloud-based and accessible via the communication network 410.

The data analytics system 416 may store the sleep times for the person being monitored in the database 426. In some embodiments, the controller 420 may query the data analytics system 416 via the network interface 408 for the sleep times to control the lighting system 422. The sleep times may specify ranges of times that the person is usually asleep. For example, the controller 420 may send an HTTP request to obtain these sleep times and the data analytics system 416 may respond with these sleep times. The HTTP request may identify the person being monitored via the device ID associated with the controller 420 and the data analytics system 416 may use the device ID to access the sleep times for the person and provide them to the controller 420. The controller 420 may turn on and off the lights of the lighting system 422 based on the sleep times.

For example, the clock 434 may provide the microprocessor 404 with a time of day. The microprocessor 404 may compare the time of day to whether the person should be asleep according to the sleep times. If the time of day is within the times that the person should be asleep, then the microprocessor 404 may turn on and off the lights based on the type of movement of the person. Otherwise, if the time of day is not within the sleep pattern, then the microprocessor 404 may not turn on and off the lights based on the type of movement since the person likely is not asleep.

In other arrangements, the data analytics system 416 may query the controller 420 for data associated with the types of movements detected by the controller 420. For instance, the data analytics system 416 may query to determine whether a person is lying down on the bed. The controller 420 may respond to the query with an indication as to whether the person is lying down on the bed. In this regard, the controller 420 might not proactively provide the type of movement to the data analytics system 416.

The user interface 424 may be a web application, a mobile application on a mobile device, or an online dashboard to the data analytics system 416. The user interface 424 may be used to review and analyze habits of the person being monitored. For instance, the microprocessor 404 may send messages to the data analytics system 416 to indicate the type of movement that the microprocessor 404 detects on the bed. The messages may take the form of HTTP messages in some examples that specify to the data analytics system 416 that the person is lying down on the bed, is not on the bed, is sitting up on the bed, or is rolling around on the bed. Additionally, the HTTP messages may indicate a timestamp based on the clock 434 indicating a time of the movement. The data analytics system 416 may store these messages for later analysis, for example, to determine a frequency of the person getting out of bed over a period of time, which can then be reviewed on the user interface 424.

Based on the messages from the microprocessor 404, the data analytics system 416 may periodically monitor a duration that the person takes to return to the bed after leaving the bed. For example, the duration may be a difference between a time of the time stamp in the message indicating a person has left a bed and the time of the timestamp in the message when the person returns back to the bed. Alternatively, the clock 432, e.g., timer, may be used to determine the duration. For example, when a message indicates that a person has left his bed, then a timer may be started to time how long the person takes before he returns back to the bed. When the person does return, indicated by a message from the microprocessor 404, then the timer may be stopped. The time indicated by the timer may be the duration of time the person takes to return to the bed after leaving the bed. When the person returns to the bed, the data analytics system 416 may end the monitoring and log the duration in the database 426 for later review and analysis.

The duration of time may be compared to a standard duration. This standard duration may be an average of durations of time that the person takes from leaving the bed to returning back to the bed. Alternately, this standard duration may have been input into the database 426 via the user interface 424. This comparison may be used to assess a future likelihood that the person may fall or be injured because of the time he or she may take to return back to bed.

Additionally, these messages may be used to signal alerts. If no message is received from the microprocessor 404 that indicates that the person has returned back to his bed after a programmable reference time interval, then the data analytics system 416 may send an alert. For example, when a message indicates that a person has left his bed, then a timer may be started on the data analytics system 416. If the time on the timer exceeds the reference time interval, then this may indicate that the person may not be able to get back to the bed, because he or she may have fallen and is not mobile. The alert sent by the data analytics system 416 may identify the person being monitored and the data analytics system 416 may identify the caregiver responsible for the person. The data analytics system 416 may send the alert to a device such as a mobile phone or a computer of the caregiver to notify the caregiver of the condition of the person.

Figure 4:
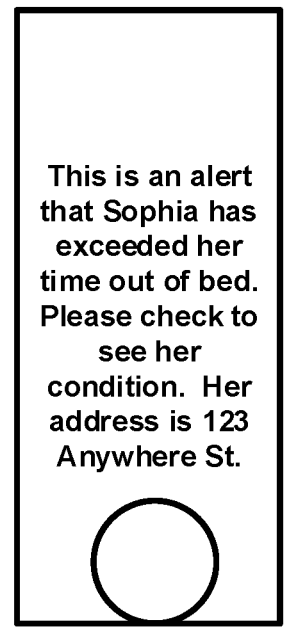
FIG. 4 illustrates an example alert.

FIG. 4 shows an example of this alert as shown on a mobile phone. The alert may be a text message, alarm, e-mail, pager, interactive voice mail and the like, to indicate that the person being monitored has been out of the bed for an extended period of time. The reason for the alert may be that this person may have fell and/or is immobile and therefore cannot get back into bed. The alert may also provide a mechanism to check up on the person, such as an address or phone number. This way a caregiver who receives the alert can check on the well-being of the person being monitored. The alert may also be stored in the database 426 for later review and analysis.

In other embodiments, the microprocessor 404, rather than the data analytics system 416, may monitor the duration that the person takes to return to the bed after leaving the bed. If the duration exceeds the standard duration, the microprocessor 404 may send an alert to the data analytics system 416 and the data analytics system 416 may provide the appropriate notification to the user interface 424.

Based on an analysis of the messages from the microprocessor 404, the user interface 424 may present reports to show trends of nighttime activity and the history of alerts sent out in the past. The trends may include duration of time a person is out of bed and number of times that a person gets out bed on a given night. This may allow caregivers to monitor activity and be aware if the person's activity has deviated from his or her usual pattern or averages for a facility, thereby indicating possible health issues or a higher likelihood that the person may fall. Further, the user interface 424 may allow customized settings for the person being monitored, such as the sensor values indicative of lying down on the bed, sitting up in bed, rolling around on the bed, and being out of bed, the standard duration for a person to go from getting out of bed to returning to bed, the reference time interval for triggering an alert, the sleep time of the person, who to send an alert to, a caregiver contact information and the like. These settings may be input to the controller 420 and/or data analytics system 416 by a caregiver or facility, for example. Additionally, one or more of these customized settings may be stored in the database 426 according to device ID (or some other identifying characteristic). Then, the microprocessor 404 or data analytics system 416 can provide the device ID to access the data for a person being monitored associated with the device ID. Additionally, or alternatively, the customized settings may be stored on the controller 420.

Further, the data analytics system 416 may allow determination and presentation on the user interface 424 of aggregated data collected from various controllers 420 associated with different persons being monitored. The aggregated data may not be individual specific. For example, the aggregated data may include an average number of alerts received for a care facility over a period of time, an average number of time, e.g., frequency, that residents in a care facility get out of bed and return to bed during their sleep times, an average duration for getting out of the bed to lying down on the bed for the residents, and/or an average number of times that that residents in a care facility get out of bed and return to bed during their sleep times. The aggregated data may also correlate age of the person to the number of times the person gets in and out of bed. These are just some examples of data that may analyzed by the data analytics system 416.

Further, the data analytics system 416 may receive messages from the microprocessor 404 relating to triggering of sensors other than sensor 402. For instance, the controller 420 may be coupled to a voice sensor or motion sensor. The microprocessor 404 may indicate that the voice sensor has been activated or the motion sensor has been activated. These activations may cause an alert to be generated. Still further, the microprocessor 404 may indicate that a voltage level of a battery in the lighting system has dropped to a certain level. The light circuit 412 of the lighting system 422 may have a microcontroller to monitors the voltage level of the light batteries. If the voltage level drops below a threshold, the light circuit 412 may signal the controller 420 of the low battery and the microprocessor 404 may send a message to the data analytics system 416 to cause an alert for a caregiver to replace a battery.

In other embodiments, the microprocessor 404 may send messages having the actual signal level of the sensor 402 rather than simply an indication of, e.g., whether the person is on the bed or not on the bed. The actual signal levels may enable the data analytics system 416 to determine more granular types of movement of the person on the bed, such as respiration rate and heart rate. These other messages may be sent periodically during the sleep time of the person.

Additionally, the user interface 424 may enable pushing software via the communication 410 to the controller 420. The software may enable updating the functionality of the controller 420.

Figure 5:
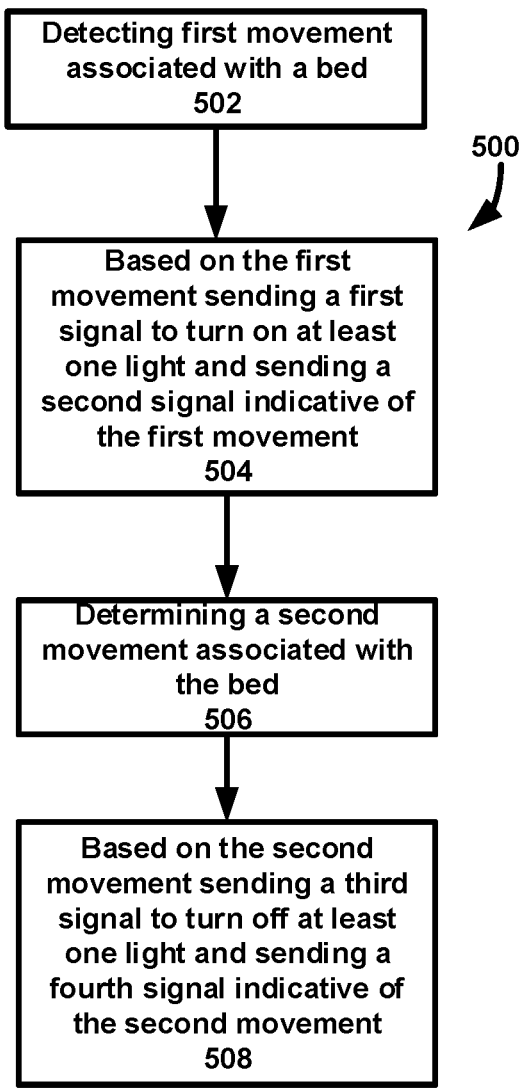
FIG. 5 illustrates a flow diagram showing an example operation of the presence-based illumination and analytics system.

FIG. 5 presents an embodiment of a method that can be implemented within the disclosed operating environment. The method and the other process disclosed herein may include one or more operations, functions, or actions. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

In addition, for the method in FIG. 5 and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device. In addition, for the method 500 and other processes and methods disclosed herein, each block in FIG. 5 may represent circuitry that is wired to perform the specific logical functions in the process.

FIG. 5 illustrates a flow diagram 500 showing an example operation of the presence-based illumination and analytics system from the perspective of the controller 420. At 502, a first movement associated with a bed is detected. For instance, the first movement may be that the sensor 402 indicates that a person is not on the bed. At 504, based on the first movement, a first signal is sent to turn on the lighting system 422. Additionally, at 504, a second signal indicative of the first movement is sent. For example, this second signal may be sent to the data analytics system 416 so that the data analytics may monitor duration of time a person is not on the bed. At 506, a second movement associated with the bed is detected. For instance, the second movement may be that the sensor 402 indicates that the person is sleeping on the bed. At 508, based on the second movement, a third signal is sent to turn off the lighting system 422. Additionally, at 508, a fourth signal indicative of the second movement is sent. For example, this fourth signal may be sent to the data analytics system 416 so that with the second signal, the data analytics may determine a duration of time that the person is not in bed.

Figure 6:
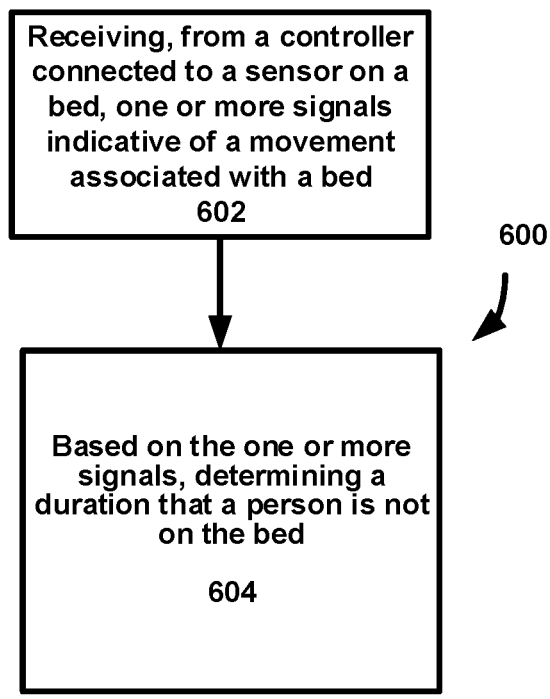
FIG. 6 illustrates another flow diagram showing an example operation of the presence-based illumination and analytics system.

FIG. 6 illustrates another flow diagram 600 showing an example operation of the presence-based illumination and analytics system from the perspective of the data analytics system 416. At 602, one or more signals indicative of a movement associated with a bed is received from a controller connected to a sensor on a bed. The signals may include HTTP messages which indicate that the person is on the bed or not on the bed. At 604, a determination is made based on the one or more signals, of a duration that a person is not on the bed. For instance, based on the signals indicative of movement, a timer may be started. The timer may monitor how long the person may take until returning back to the bed, as indicated by the one or more signals. As another example, a determination could be made that the duration of time indicated by the timer exceeds a customized threshold amount. In this case, an alert may be sent based on the duration of time exceeding the threshold amount. This alert may be to the caretaker to warn a probability of a fall of the monitored person thereby providing and ensuring the safety of person. Further, the data analytics system 416 may store the duration and/or alerts in a database. This will allow caregivers to monitor activity and be aware if the person's activity has deviated from the usual pattern, thereby indicating possible health issues.

The description above discloses, among other things, various example systems, methods, apparatus, and articles of manufacture including, among other components, firmware and/or software executed on hardware. It is understood that such examples are merely illustrative and should not be considered as limiting. For example, it is contemplated that any or all of the firmware, hardware, and/or software aspects or components can be embodied exclusively in hardware, exclusively in software, exclusively in firmware, or in any combination of hardware, software, and/or firmware. Accordingly, the examples provided are not the only way(s) to implement such systems, methods, apparatus, and/or articles of manufacture.

Additionally, references herein to "embodiment" means that a particular feature, structure, or characteristic described in connection with the embodiment can be included in at least one example embodiment of an invention. The appearances of this phrase in various places in the specification are not necessarily all referring to the same embodiment, nor are separate or alternative embodiments mutually exclusive of other embodiments. As such, the embodiments described herein, explicitly and implicitly understood by one skilled in the art, can be combined with other embodiments.

The specification is presented largely in terms of illustrative environments, systems, procedures, steps, logic blocks, processing, and other symbolic representations that directly or indirectly resemble the operations of data processing devices coupled to networks. These process descriptions and representations are typically used by those skilled in the art to most effectively convey the substance of their work to others skilled in the art. Numerous specific details are set forth to provide a thorough understanding of the present disclosure. However, it is understood to those skilled in the art that certain embodiments of the present disclosure can be practiced without certain, specific details. In other instances, well known methods, procedures, components, and circuitry have not been described in detail to avoid unnecessarily obscuring aspects of the embodiments. Accordingly, the scope of the present disclosure is defined by the appended claims rather than the forgoing description of embodiments.

When any of the appended claims are read to cover a purely software and/or firmware implementation, at least one of the elements in at least one example is hereby expressly defined to include a tangible, non-transitory medium such as a memory, DVD, CD, Blu-ray, and so on, storing the software and/or firmware.

To the extent that examples described herein involve operations performed or initiated by actors, such as "humans", "operators", "users" or other entities, this is for purposes of example and explanation only. The claims should not be construed as requiring action by such actors unless explicitly recited in the claim language.

We claim:
1. A method comprising:
    detecting, by a controller, a first movement associated with a bed;
    based on the first movement, sending, by the controller, a first signal over a first network interface of the controller to turn on at least one wireless communication-enabled light and sending, by the controller, a second signal indicative of the first movement over a second network interface of the controller to a data analytics system;
    detecting, by the controller, a second movement associated with the bed;
    based on the second movement, sending, by the controller, a third signal over the first network to turn off the at least one wireless communication-enabled light and sending, by the controller, a fourth signal indicative of the second movement over the second network interface to the data analytics system; and
determining, by the data analytics system, based on the second signal and the fourth signal, that a person is not on the bed.

2. The method of claim 1, wherein detecting the first movement comprises determining that a person is not on the bed and detecting the second movement comprises determining that the person is on the bed.

3. The method of claim 2, wherein sending the second and fourth signal results in a determination, by the data analytics system, of a duration of time that the person is not on the bed based on the second and fourth signals.

4. The method of claim 1, wherein the second signal is indicative of a person not on the bed and the fourth signal is indicative of the person on the bed.

5. The method of claim 1, wherein the second signal further defines a time associated with the first movement and wherein the fourth signal further defines a time associated with the second movement.

6. The method of claim 1, wherein sending the second signal comprises sending, by the controller and to the data analytics system, the second signal over a network for storage in a database of the data analytics system.

7. The method of claim 1, wherein sending the second signal results in a determination, by the data analytics system, of a frequency of times that a person gets up from the bed and returns back to the bed.

8. A device comprising:
a first network interface;
a second network interface;
a processor; and
a memory storing instructions that, when executed, cause the processor to:
    detect, by a sensor on a bed, a first signal indicative of a first movement associated with the bed;
    based on the first movement, send a first signal over the first network interface to turn on at least one wireless-communication-enabled light and send a second signal indicative of the first movement to a data analytics system over the second network interface;
    detect, by the sensor on the bed, a second signal indicative of a second movement associated with the bed;
    based on the second movement, send a third signal over the first network interface to turn off the at least one wireless communication-enabled light and send a fourth signal indicative of the second movement over the second network to the data analytics system,
    wherein sending the second signal and the fourth signal causes the data analytics system to:
        determine a duration that a person is not on the bed.

9. The device of claim 8, wherein the instructions that cause the processor to detect the first signal comprise instructions that, when executed, cause the processor to:
determine that the person is not on the bed.

10. The device of claim 8, wherein the device causes the data analytics system to send an alert when the duration exceeds a threshold amount.

11. The device of claim 8,
wherein the second signal is indicative of a person not on the bed and the fourth signal is indicative of the person on the bed.

12. The device of claim 8, wherein the second signal further defines a time associated with the first movement and wherein the fourth signal further defines a time associated with the second movement.

13. A system comprising:
at least one wireless communication-enabled light;
a data analytics system comprising:
    a processor; and
    a memory storing instructions thereon;
a controller comprising:
    a first interface for sending signals to the data analytics system via a first network;
    a second interface for sending signals to the at least one wireless communication-enabled light over a second wireless network; and
    a processor; and
    a memory storing instructions that, when executed, cause the processor of the controller to:
        detect a first movement associated with a bed;
        based on the first movement, send a first signal over the first network to turn on the at least one wireless communication-enabled light and send a second signal indicative of the first movement over the second network to the data analytics system;
        detect a second movement associated with the bed; and
        based on the second movement, send a third signal over the first network to turn off the at least one wireless communication-enabled light and send a fourth signal indicative of the second movement over the second network to the data analytics system,
    wherein the memory of the data analytics system stores instructions that, when executed, cause the processor of the data analytics system to:
        determine, based on the second signal and the fourth signal, that a person is not on the bed.

14. The system of claim 13, wherein the instructions that, when executed, cause the processor of the controller to detect the first movement comprise instructions that, when executed, cause the processor of the controller to determine that a person is not on the bed, and wherein the instructions that, when executed, cause the processor of the controller to detect the second movement comprise instructions that, when executed, cause the processor of the controller to determine that the person is on the bed.

15. The system of claim 14, wherein the data analytics system further comprises instructions that, when executed, cause the processor of the data analytics system to:
determine a duration of time that the person is not on the bed based on the second and fourth signals.

16. The method of claim 1, the method comprising:
obtaining, by the data analytics system, a threshold time value, wherein the threshold time value is indicative of a maximum duration of time that a person is allowed not to be on the bed;
determining, by the data analytics system, that there is no person on the bed;
after determining that there is no person on the bed:
    determining, by the data analytics system, a duration of time that has elapsed since no person was determined to be on the bed;
    determining, by the data analytics system, that the duration of time that has elapsed exceeds the threshold time value; and
    after determining that the elapsed time exceeds the threshold time value:
        generating, by the data analytics system, an alert, wherein the alert indicates that the time that has elapsed since no person was determined to be on the bed is greater than the threshold time value.

17. The device of claim 8, wherein sending the second signal and the fourth signals further causes the data analytics system to:
- obtain a threshold time value, wherein the threshold time value is indicative of a maximum duration of time that a person is allowed not to be on the bed;
- determine that there is no person on the bed;
- after determining that no person is on the bed:
  - determine a duration of time that has elapsed since no person was determined to be on the bed;
  - determine whether the duration of time that has elapsed exceeds the threshold time value; and
  - after determining that the elapsed time exceeds the threshold time value:
    - generate an alert, wherein the alert indicates that the time that has elapsed since no person was determined to be on the bed is greater than the threshold time value.

18. The system of claim 13, wherein the memory of the data analytics system comprises instructions that, when executed, cause the processor of the data analytics system to:
- obtain a threshold time value, wherein the threshold time value is indicative of a maximum duration of time that a person is allowed not to be on the bed;
- determine a duration of time that has elapsed since no person was determined to be on the bed;
- after determining that there is no person on the bed:
  - determine a duration of time that has elapsed since no person was determined to be on the bed;
  - determine whether the duration of time that has elapsed exceeds the threshold time value; and
  - after determining that the elapsed time exceeds the threshold time value:
    - generate an alert, wherein the alert indicates that the time that has elapsed since no person was determined to be on the bed is greater than the threshold time value.

19. The system of claim 13, wherein the data analytics system causes a computing device to generate a graphical user interface (GUI), wherein the GUI comprises a visual representation of at least the first movement.

20. The device of claim 10,
- wherein the alert identifies a person associated with the bed, and
- wherein the alert causes the data analytics system to send the alert to a caregiver assigned to the identified person, and
- wherein the caregiver is assigned to the identified person by the data analytics system.

* * * * *